United States Patent [19]

Szczepanski et al.

[11] Patent Number: 4,523,947

[45] Date of Patent: Jun. 18, 1985

[54] USE OF TRIAZINE DERIVATIVES FOR PROTECTING MAIZE AND SORGHUM PLANTS

[75] Inventors: Henry Szczepanski, Wallbach; Dagmar Berrer, Riehen, both of Switzerland

[73] Assignee: Ciba-Geigy Corporation, Ardsley, N.Y.

[21] Appl. No.: 615,021

[22] Filed: May 29, 1984

[30] Foreign Application Priority Data

Jun. 6, 1983 [CH] Switzerland ............... 3085/83

[51] Int. Cl.³ .................................. A01N 43/66
[52] U.S. Cl. ............................ 71/93; 544/194; 544/216; 544/180; 544/211
[58] Field of Search .................................. 71/93

[56] References Cited

PUBLICATIONS

Wegler, "Chemie der Pflanzenschutz- und Schädlings-bekämpfungsmittel" 8, 91–93, 322–327, (1982).

Primary Examiner—John M. Ford
Attorney, Agent, or Firm—Edward McC. Roberts; Frederick H. Rabin

[57] ABSTRACT

There are described triazine derivatives of the formula I

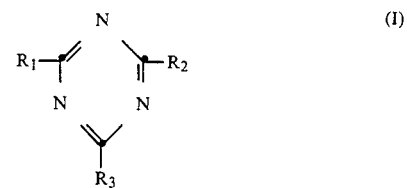

wherein $R_1$, $R_2$ and $R_3$ independently of one another are each $C_1$–$C_5$-alkyl which is unsubstituted or monosubstituted by $C_3$–$C_6$-cycloalkyl, or mono- or polysubstituted by halogen, or is $C_3$–$C_6$-cycloalkyl which is unsubstituted or mono- or polysubstituted by halogen, or one of the substituents $R_1$, $R_2$ and $R_3$ is also halogen or —$NR_4R_5$, in which $R_4$ is hydrogen or $C_1$–$C_5$-alkyl and $R_5$ is hydrogen, $C_1$–$C_5$-alkyl, monochloroacetyl or dichloroacetyl. The triazine derivatives are used for the protection of maize and sorghum plants against the harmful effects of herbicidal chloroacetanilides and chloroacetamides.

10 Claims, No Drawings

USE OF TRIAZINE DERIVATIVES FOR PROTECTING MAIZE AND SORGHUM PLANTS

The present invention relates to the use of triazine derivatives for protecting maize and sorghum plants against the harmful effects of herbicidal chloroacetanilides and chloroacetamides, to compositions containing such triazine derivatives and to novel triazine derivatives.

With the use of herbicidal chloroacetanilides and chloroacetamides, maize and sorghum plants can to a certain extent suffer damage depending on such factors as for example the dosage level and the mode of application, nature of the soil and climatic conditions, for example: time of exposure to light, temperature and rainfall. Damage can occur both as a result of a specific herbicidal treatment of these cultivated plants and as a result of drifting or seepage of the herbicides during or after the treatment of adjacent areas within reach of the maize and sorghum crops, and also in consequence of herbicide residues in the soil.

It has now been found that surprisingly a group of triazine derivatives is excellently suitable for protecting maize and sorghum plants against the harmful effects of herbicidal chloroacetanilides and chloroacetamides. These triazine derivatives are therefore to be designated in the following as 'antidotes' or 'safeners'.

Triazine derivatives which are suitable for protecting maize and sorghum plants against the harmful effects of herbicidal chloroacetanilides and chloroacetamides correspond to the formula I

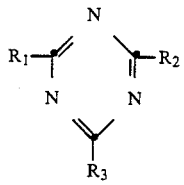

wherein $R_1$, $R_2$ and $R_3$ independently of one another are each $C_1$–$C_5$-alkyl which is unsubstituted or monosubstituted by $C_3$–$C_6$-cycloalkyl, or mono- or polysubstituted by halogen, or is $C_3$–$C_6$-cycloalkyl which is unsubstituted or mono- or polysubstituted by halogen, or one of the substituents $R_1$, $R_2$ and $R_3$ is also halogen or —$NR_4R_5$, in which $R_4$ is hydrogen or $C_1$–$C_5$-alkyl and $R_5$ is hydrogen, $C_1$–$C_5$-alkyl, monochloroacetyl or dichloroacetyl.

$C_1$–$C_5$-Alkyl embraces straight-chain and branched-chain alkyl groups, for example: methyl, ethyl, n-propyl, isopropyl, iso-butyl, sec-butyl, tert-butyl, n-pentyl, and isomers thereof.

$C_3$–$C_6$-Cycloalkyl is cyclopropyl, cyclobutyl, cyclopentyl and cyclohexyl.

By halogen, as substituent or part of a substituent, is meant in this case fluorine, chlorine, bromine and iodine, preferably chlorine.

Haloalkyl denotes monohalogenated to perhalogenated alkyl substituents, for example —$CH_2Br$, —$CHF_2$, —$CHCl_2$, —$CH_2J$, —$CH_2CCl_3$, —$CH_2CH_2Cl$, —$CH_2CH_2CF_3$, —$CH_2CH_2CH_2Br$, —$CH_2CHClCH_2Cl$, —$CH_2CH_2CH_2Br$, —$CCl_2CCl_3$, $CF_3$ and in particular —$CH_2Cl$, —$CH_2CH_2CH_2Cl$, —$CH_2CH_2CH_2CH_2Cl$ and —$CCl_3$.

Compounds of the formula I which are especially suitable for application according to the invention are those in which two of the substituents $R_1$, $R_2$ and $R_3$ independently of one another are each $C_1$–$C_5$-alkyl which is unsubstituted or monosubstituted by $C_3$–$C_6$-cycloalkyl, particularly cyclopropyl, or mono- or polysubstituted by halogen, or are $C_3$–$C_6$-cycloalkyl which is unsubstituted or mono- or polysubstituted by halogen, or one of the substituents is also halogen, and the third substituent is $C_3$–$C_6$-cycloalkyl, especially cyclopropyl.

Individual compounds very well suited for use according to the invention are:

2-methyl-4,6-bis(trichloromethyl)-s-triazine,
2-chloromethyl-4,6-bis(trichloromethyl)-s-triazine,
2-amino-4-chloromethyl-6-trichloromethyl-s-triazine,
2-(3-chloro-n-propyl)-4-methyl-6-trichloromethyl-s-triazine,
2-(3-chloro-n-propyl)-4-cyclopropyl-6-trichloromethyl-s-triazine,
2-(4-chloro-n-butyl)-4,6-bis(trichloromethyl)-s-triazine,
2-amino-4-(3-chloro-n-propyl)-6-trichloromethyl-s-triazine,
2-cyclopropyl-4,6-bis(trichloromethyl)-s-triazine,
2-amino-4-cyclopropyl-6-trichloromethyl-s-triazine,
2-(3-chloro-n-propyl)-4,6-bis(trichloromethyl)-s-triazine,
2-ethyl-4-(3-chloro-n-propyl)-6-trichloromethyl-s-triazine,
2-(3-chloro-n-propyl)-4-n-propyl-6-trichloromethyl-s-triazine,
2-amino-4-cyclopropyl-6-methyl-s-triazine,
2-(chloroacetyl)-amino-4-(3-chloro-n-propyl)-6-methyl-s-triazine,
2-amino-4,6-dimethyl-s-triazine,
2-(dichloroacetyl)-amino-4-(3-chloro-n-propyl)-6-methyl-s-triazine,
2-ethylamino-4-chloro-6-[N-ethyl-N-(dichloroacetyl)amino]-s-triazine,
2-methylamino-4-cyclopropyl-6-trichloromethyl-s-triazine,
2-ethylamino-4-cyclopropyl-6-trichloromethyl-s-triazine,
2-n-propylamino-4-cyclopropyl-6-trichloromethyl-s-triazine,
2-isopropylamino-4-cyclopropyl-6-trichloromethyl-s-triazine,
2-dimethylamino-4-cyclopropyl-6-trichloromethyl-s-triazine,
2-amino-4,6-bis(trichloromethyl)-s-triazine,
2-chloro-4,6-bis(trichloromethyl)-s-triazine,
2-ethylamino-4,6-bis(trichloromethyl)-s-triazine,
2,4,6-tris(trichloromethyl)-s-triazine,
2-methyl-4-methylamino-6-trichloromethyl-s-triazine,
2-amino-4-methyl-6-trichloromethyl-s-triazine,
2-isopropyl-4,6-bis(trichloromethyl)-s-triazine,
2-ethyl-4,6-bis(trichloromethyl)-s-triazine,
2-amino-4-dichloromethyl-6-methyl-s-triazine, and
2-amino-4-cyclopropyl-6-dichloromethyl-s-triazine.

Substances to be antagonised are in particular chloroacetanilides which exhibit herbicidal activity and correspond to the formula II

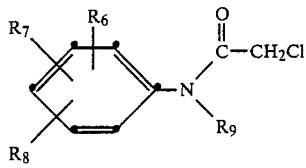

wherein
R$_6$ is hydrogen, C$_1$-C$_4$-alkyl, methoxy or chlorine, R$_7$ is hydrogen or C$_1$-C$_3$-alkyl, and R$_8$ is hydrogen, methyl or ethyl, with the proviso that R$_6$, R$_7$ and R$_8$ together do not contain more than 6 carbon atoms, and R$_9$ is ethyl, isopropyl, 1-methyl-2-methoxyethyl, —CH$_2$—R$_{10}$, —CH(CH$_3$)—R$_{11}$, —CH$_2$—CH(R$_{12}$)—R$_{13}$, —CH(CH$_3$)—CH(R$_{14}$)—R$_{15}$, C$_3$-C$_4$-alkynyl or 5-methyl-1,3,4-oxadiazol-2-yl, in which R$_{10}$ is C$_1$-C$_4$-alkoxy, C$_1$-C$_3$-alkoxycarbonyl, dimethylaminocarbonyl, 2-propynylaminocarbonyl, benzoyl, 4-chlorobenzoyl, cyano, 2-furanyl, 2-tetrahydrofuranyl, 1,3-dioxolan-2-yl, 1,3-dioxan-2-yl, 1H-pyrazol-1-yl, 3,5-dimethyl-1H-pyrazol-1-yl, 1H-1,2,4-triazol-1-yl, 1-methyl-5-methylthio-1,3,4-triazol-2-yl or —P(O)(OR$_{16}$)(OR$_{17}$), in which R$_{16}$ and R$_{17}$ independently of one another are each methyl or ethyl, R$_{11}$ is methoxycarbonyl or 1,3-dioxolan-2-yl, R$_{12}$ is hydrogen, and R$_{13}$ is C$_1$-C$_4$-alkoxy or allyloxy, or R$_{12}$ is methyl and R$_{13}$ is C$_1$-C$_2$-alkoxy, or R$_{12}$ and R$_{13}$ is ethoxy and R$_{14}$ is hydrogen and R$_{15}$ is C$_1$-C$_2$-alkoxy, or R$_{14}$ is methyl and R$_{15}$ is methoxy.

Further substances to be antagonised are herbicidally active chloroacetamides, especially compounds of the formula III

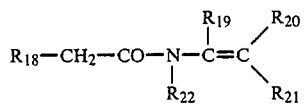

wherein R$_{18}$ is chlorine, R$_{19}$ is C$_1$-C$_4$-alkyl, R$_{20}$ and R$_{21}$ independently of one another are each hydrogen or C$_1$-C$_4$-alkyl, the substituents R$_{19}$, R$_{20}$ and R$_{21}$ together containing 2 to 8 carbon atoms, and R$_{22}$ is alkoxyalkyl having 2 to 6 carbon atoms, and in particular N-(1-isopropyl-2-methyl-1-propen-1-yl)-N-(methoxyethyl)-chloroacetamide.

Herbicidally effective chloroacetanilides to be antagonised are in particular the following:

H-1. N-chloroacetyl-N-(2-methoxy-1-methylethyl)-2,6-diethylaniline,
H-2. N-chloroacetyl-N-(2-methoxy-1-methylethyl)-2-ethyl-6-methylaniline,
H-3. N-(2-ethoxyethyl)-N-chloroacetyl-2,6-diethylaniline,
H-4. N-chloroacetyl-N-(2-n-propoxyethyl)-2-ethyl-6-methylaniline,
H-5. N-chloroacetyl-N-(2-n-propoxyethyl)-2,6-diethylaniline,
H-6. N-chloroacetyl-N-(2-isopropoxyethyl)-2-ethyl-6-methylaniline,
H-7. N-ethoxycarbonylmethyl-N-chloroacetyl-2,6-dimethylaniline,
H-8. N-ethoxycarbonylmethyl-N-chloroacetyl-2,6-diethylaniline,
H-9. N-chloroacetyl-N-methoxycarbonylmethyl-2,6-dimethylaniline,
H-10. N-chloroacetyl-N-(2,2-diethoxyethyl)-2,6-dimethylaniline,
H-11. N-chloroacetyl-N-(2-methoxy-1-methylethyl)-2,3-dimethylaniline,
H-12. N-(2-ethoxyethyl)-N-chloroacetyl-2-methylaniline,
H-13. N-chloroacetyl-N-(2-methoxyethyl)-2-methylaniline,
H-14. N-chloroacetyl-N-(2-methoxy-2-methylethyl)-2,6-dimethylaniline,
H-15. N-(2-ethoxy-2-methylethyl)-N-chloroacetyl-2-ethyl-6-methylaniline,
H-16. N-chloroacetyl-N-(1-ethyl-2-methoxyethyl)-2,6-dimethylaniline,
H-17. N-chloroacetyl-N-(2-methoxyethyl)-2-methoxy-6-methylaniline,
H-18. N-n-butoxymethyl-N-chloroacetyl-2-tert-butylaniline,
H-19. N-chloroacetyl-N-(2-ethoxyethyl-1-methylethyl)-2,6-dimethylaniline,
H-20. N-chloroacetyl-N-(2-methoxyethyl)-2-chloro-6-methylaniline,
H-21. N-(2-ethoxyethyl)-N-chloroacetyl-2-chloro-6-methylaniline,
H-22. N-(2-ethoxyethyl)-N-chloroacetyl-2,3,6-trimethylaniline,
H-23. N-chloroacetyl-1-(2-methoxyethyl)-2,3,6-trimethylaniline,
H-24. N-chloroacetyl-N-cyanomethyl-2,6-dimethylaniline,
H-25. N-but-3-in-1-yl-N-chloroacetylaniline,
H-26. N-chloroacetyl-N-propargyl-2-ethyl-6-methylaniline,
H-27. N-chloroacetyl-N-(1,3-dioxolan-2-ylmethyl)-2,6-dimethylaniline,
H-28. N-chloroacetyl-N-(1,3-dioxolan-2-ylmethyl)-2-ethyl-6-methylaniline,
H-29. N-chloroacetyl-N-(1,3-dioxan-2-ylmethyl)-2-ethyl-6-methylaniline,
H-30. N-chloroacetyl-N-(2-furanylmethyl)-2,6-dimethylaniline,
H-31. N-chloroacetyl-N-(2-furanylmethyl)-2-ethyl-6-methylaniline,
H-32. N-chloroacetyl-N-(2-tetrahydrofuranylmethyl)-2,6-dimethylaniline,
H-33. N-chloroacetyl-N-(N-propargylcarbamoylmethyl)-2,6-dimethylaniline,
H-34. N-ethoxymethyl-N-chloroacetyl-2-ethyl-6-methylaniline,
H-35. N-chloroacetyl-N-methoxymethyl-2,6-diethylaniline,
H-36. N-chloroacetyl-N-(2-methoxyethyl)-2,6-dimethylaniline,
H-37. N-(2-allyloxyethyl)-N-chloroacetyl-2,6-dimethylaniline,
H-38. N-chloroacetyl-N-(2-n-propoxyethyl)-2,6-dimethylaniline,
H-39. N-chloroacetyl-N-(2-isopropoxyethyl)-2,6-dimethylaniline,
H-40. N-chloroacetyl-N-(2-methoxyethyl)-2-ethyl-6-methylaniline,
H-41. N-chloroacetyl-N-(methoxyethyl)-2,6-diethylaniline,
H-42. N-(2-ethoxyethyl)-N-chloroacetyl-2-ethyl-6-methylaniline,
H-43. N-chloroacetyl-N-(2-methoxy-1-methylethyl)-2-methylaniline,
H-44. N-chloroacetyl-N-(2-methoxy-1-methylethyl)-2,6-dimethylaniline, H-45. N-chloroacetyl-N-(N,N-dimethylcarbamoylmethyl)-2,6-dimethylaniline, H-46. N-(n-butoxymethyl)-N-chloroacetyl-2,6-diethylaniline, H-47. N-(2-n-butoxyethyl)-N-chloroacetyl-2,6-diethylaniline, H-48. N-chloroacetyl-N-(2-methoxy-1,2-dimethylethyl)-2,6-dimethylaniline, H-49. N-chloroacetyl-N-isopropyl-2,3-dimethylaniline, H-50. N-chloroacetyl-N-isopropyl-2-chloroaniline, H-51. N-chloroacetyl-N-(1H-pyrazol-1-ylmethyl)-2,6-dimethylaniline, H-52. N-chloroacetyl-N-(1H-pyrazol-1-ylmethyl)-2-ethyl-6-methylaniline, H-53. N-chloroacetyl-N-(1H-1,2,4-triazol-1-ylmethyl)-2,6-dimethylaniline, H-54. N-chloroacetyl-N-(1H-1,2,4-triazol-1-ylmethyl)-2,6-diethylaniline, H-55. N-benzoylmethyl-N-chloroacetyl-2,6-dimethylaniline, H-56. N-benzoylmethyl-N-chloroacetyl-2-ethyl-6-methylaniline, H-57. N-chloroacetyl-N-(5-methyl-1,3,4-oxadiazol-2-yl)-2,6-diethylaniline, H-58. N-chloroacetyl-N-(5-methyl-1,3,4-oxadiazol-2-yl)-2-ethyl-6-methylaniline, H-59. N-chloroacetyl-N-(5-methyl-1,3,4-oxadiazol-2-yl)-2-tert-butylaniline, H-60. N-chloroacetyl-N-(4-chlorobenzoylmethyl)-2,6-dimethylaniline, and H-61. N-chloroacetyl-N-(3-methylthio-4-methyl-1,2,4-triazol-5-ylmethyl)-2,6-diethylaniline;

particularly the chloroacetanilides Nos. H-2, H-5, H-35 and H-44.

It is possible by application of compounds of the formula I to protect maize and sorghum plants also against haloacetanilides which are described in R. Wegler, "Chemie der Pflanzenschutz- und Schädlingsbekämpfungsmittel" (Chemistry of Plant Protecting and Pesticidal Agents) Springer-Verlag (Publishers), Heidelberg, N.Y., 1982, pp. 90–93 and 322–327.

Processes for producing compounds of the formulae II and III are known, or these compounds can be produced by methods analogous to known methods.

A suitable process for protecting maize and sorghum plants by the use of compounds of the formula I comprises treating the maize or sorghum plants or the seed of these plants, or soils intended for the cultivation of maize or sorghum, before or after introduction of the vegetable material into the soil, with a compound of the formula I or with a composition containing such as compound. The treatment can be carried out before, simultaneously with or after the application of the herbicide.

The invention relates also to a process for the selective controlling of weeds in crops of maize and sorghum, in which process the maize or sorgum crops, the seed of these plants, or cultivated areas for the said cultivated plants, are treated with a herbicidal chloroacetanilide or chloroacetamide and a compound of the formula I, or with a composition containing a combination of such a herbicide and a compound of the formula I. Compositions which contain the stated herbicide/antidote combination likewise form subject matter of the present invention.

The weeds to be controlled can be both monocotyledonous and dicotyledonous weeds.

The cultivated areas for maize or sorghum crops are those on which the cultivated plants are already growing, or areas of land sown with the seed of these cultivated plants, and also the soil intended for the growing of the said cultivated plants.

The amount of antidote to be applied in proportion to the amount of herbicide depends largely upon the type of application. In the case of a field treatment, which is carried out either with the use of a tank mixture comprising a combination of antidote and herbicide or with separate application of antidote and herbicide, the ratio of antidote to herbicide is as a rule 1:100 to 10:1, preferably 1:5 to 8:1, and particularly 1:1. With seed dressing, however, the amounts of antidote required in proportion to the amounts of herbicide per hectare of cultivated land are very much smaller. These are used for seed dressing as a rule 0.1 to 10 g of antidote per kg of seed, preferably 1 to 2 g. When the antidote is applied shortly before sowing, with seed soaking, there are advantageously used antidote solutions containing the active ingredient at a concentration of 1 to 10,000 ppm, preferably 100 to 1000 ppm.

The compounds of the formula I can be used on their own or together with inert additives and/or the herbicides.

The present application relates therefor also to compositions which contain compounds of the formula I and inert additives and/or herbicides to be antagonised.

For application, the compounds of the formula I, or combinations of compounds of the formula I with the herbicides to be antagonised, are advantageously used together with auxiliaries customarily employed in formulation practice, and are thus processed, in a known manner, for example into the form of emulsion concentrates, brushable pastes, directly sprayable or dilutable solutions, diluted emulsions, wettable powders, soluble powders, dusts or granulates, and also encapsulations in for example polymeric substances. The application processes, such as spraying, atomising, dusting, scattering, brushing or pouring, and likewise the type of composition, are selected to suit the objectives to be achieved and the given conditions.

The formulations, that is to say, the compositions or preparations containing the active ingredient of the formula I, or a combination of active ingredient of the formula I and the herbicide to be antagonised, and optionally a solid or liquid additive, are produced in a known manner, for example by the intimate mixing and/or grinding of the active ingredients with extenders, such as with solvents, solid carriers and optionally surface active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Depending on the nature of the active ingredient of the formula I to be formulated, and optionally also of the herbicide to be antagonised, suitable surface-active compounds are nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-laurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)ethylene oxide adduct, or phospholipides.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications:
"McCutcheon's Detergents and Emulsifiers Annual", MC Publishing Corp., Ridgewood, N.J., 1981, and
Stache, H., "Tensid-Taschenbuch" (Tenside Pocketbook), Carl Hanser Verlag, Munich/Vienna, 1981.

The agrochemical preparations contain as a rule 0.1 to 99% by weight, especially 0.1 to 95% by weight, of active ingredient of the formula I or of an active ingredient mixture antidote/herbicide, 1 to 99.9% by weight, particularly 5 to 99.8% by weight, of a solid or liquid additive, and 0 to 25% by weight, especially 0.1 to 25% by weight, of a tenside.

Whereas commercial products are preferably in the form of concentrated compositions, the preparations employed by the end-user are as a rule diluted.

The compositions can also contain further additives, such as stabilisers, antifoaming agents, viscosity regulators, binders and adhesives, as well as fertilisers or other active substances for obtaining special effects.

For the use of compounds of the formula I, or of compositions containing them, for the protection of cultivated plants against the harmful effects of chloroacetanilides and chloroacetamides, various methods and techniques are applicable, such as those described in the following.

(i) Seed dressing (a) Dressing of the seeds with an active ingredient of the formula I, formulated as a wettable powder, by shaking in a vessel until there is a uniform distribution over the surface of the seeds (dry dressing). The amount of active ingredient of the formula I used for this purpose is about 10 to 500 g (40 g to 2 kg of wettable powder) per 100 kg of seed.

(b) Dressing of the seeds with an emulsion concentrate of the active ingredient of the formula I according to method (a) (wet dressing).

(c) Dressing by immersion of the seed in a liquor containing 50–3200 ppm of active ingredient of the formula I for 1 to 72 hours, and optionally subsequent drying of the seed (immersion dressing).

The dressing of the seed or the treatment of the germinated yound seedlings is, in accordance with nature, the preferred method of application, because the treatment with the active ingredient is directed completely at the target growth. There are used as a rule 10 g to 500 g, preferably 50 to 250 g, of antidote per 100 kg of seed; however, depending on the method of treatment, which may render possible also the addition of other active substances or micronutrients, the stated limiting concentrations may be varied upwards or downwards (repeat dressing).

(ii) Application as tank mixture

A liquid preparation of a mixture of antidote and herbicide (quantitative ratio preferably between 10:1 and 1:10) is used, the applied amount of herbicide being 0.1 to 10 kg per hectare. This tank mixture is preferably applied before or immediately after sowing, or it is worked into the unsown soil to a depth of 5 to 10 cm.

(iii) Application into the sand furrow

The antidote is introduced, as an emulsion concentrate, wettable powder or granulate, into the open seed furrow, and, after the covering of the seed furrow in the normal manner, the herbicide is applied before the emergence of the plants.

(iv) Controlled release of active ingredient

The active ingredient of the formula I is absorbed, in solution, onto mineral granular carriers or polymerised granulates (urea/formaldehyde), and the material is allowed to dry. A coating can if required be applied (coated granules), which enables the active ingredient to be released in controlled amounts over a specific period of time.

Some of the triazine derivatives of the formula I are novel, some are known. There are thus described, inter alia, the compounds 2-methyl-4,6-bis(trichloromethyl)-s-triazine, 2-chloromethyl-4,6-bis(trichloromethyl)-s-triazine and 2-ethylamino-4-chloro-6-[N-ethyl-N-(dichloromethylcarbonyl)-amino]-s-triazine in the U.S. Pat. No. 4,340,419.

Novel triazine derivatives are for example compounds of the formula Ia embraced by the general formula I

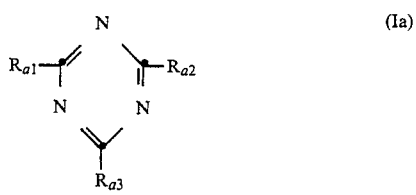
(Ia)

wherein one of the substituents $R_{a1}$, $R_{a2}$ and $R_{a3}$ is $C_1$–$C_5$-alkyl, which is unsubstituted or monosubstituted by $C_3$–$C_6$-cycloalkyl or mono- or polysubstituted by halogen, or is $C_3$–$C_6$-cycloalkyl which is unsubstituted or mono- or polysubstituted by halogen; a further of the substituents $R_{a1}$, $R_{a2}$ and $R_{a3}$ is n-pentyl or an isomer thereof, $C_1$–$C_5$-alkyl which is monosubstituted by $C_3$–$C_6$-cycloalkyl, or is $C_4$–$C_5$-alkyl which is mono- or polysubstituted by halogen, or is $C_3$–$C_6$-cycloalkyl which is unsubstituted or mono- or polysubstituted by halogen, or is an iodine atom; and the third of the substituents $R_{a1}$, $R_{a2}$ and $R_{a3}$ is $C_1$–$C_5$-alkyl which is unsubstituted or monosubstituted by $C_3$–$C_6$-cycloalkyl or mono- or polysubstituted by fluorine, bromine or iodine, or is $C_2$–$C_5$-alkyl which is mono- or polysubstituted by chlorine, or is chloromethyl, dichloromethyl, $C_3$–$C_6$-cycloalkyl which is unsubstituted or mono- or polysubstituted by halogen, or is —$NR_{a4}R_{a5}$, in which $R_{a4}$ is hydrogen or $C_1$–$C_5$-alkyl, and $R_{a5}$ is n-pentyl or an isomer thereof, monochloroacetyl or dichloroacetyl.

To be given special mention amongst these compounds are in particular those of the formula Ib embraced by the formula Ia

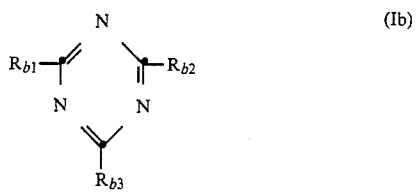
(Ib)

wherein one of the substituents $R_{b1}$, $R_{b2}$ and $R_{b3}$ is $C_1$–$C_5$-alkyl which is unsubstituted or monosubstituted by $C_3$–$C_6$-cycloalkyl or mono- or polysubstituted by halogen, or is $C_3$–$C_6$-cycloalkyl which is unsubstituted or mono- or polysubstituted by halogen; a further of the substituents $R_{b1}$, $R_{b2}$ and $R_{b3}$ is n-pentyl or an isomer thereof, $C_1$–$C_5$-alkyl which is monosubstituted by $C_3$–$C_6$-cycloalkyl, or is $C_4$–$C_5$-alkyl which is mono- or polysubstituted by halogen, or is $C_3$–$C_6$-cycloalkyl which is unsubstituted or mono- or polysubstituted by halogen, or is an iodine atom; and the third of the substituents $R_{b1}$, $R_{b2}$ and $R_{b3}$ is $C_1$–$C_5$-alkyl which is unsubstituted or monosubstituted by $C_3$–$C_6$-cycloalkyl or mono- or polysubstituted by fluorine, bromine or iodine, or is $C_2$–$C_5$-alkyl which is mono- or polysubstituted by chlorine, or is chloromethyl, dichloromethyl, $C_3$–$C_6$-cycloalkyl which is unsubstituted or mono- or polysubstituted by halogen, or is —$NR_{b4}R_{b5}$, in which $R_{b4}$ is hydrogen or $C_1$–$C_5$-alkyl, and $R_{b5}$ is n-pentyl or an isomer thereof, monochloroacetyl or dichloroacetyl, with the proviso that at least one of the substituents $R_{b1}$, $R_{b2}$ and $R_{b3}$ is $C_1$–$C_5$-alkyl which is monosubstituted by $C_3$–$C_6$-cycloalkyl, or is cycloalkyl which is unsubstituted or mono- or polysubstituted by halogen, or is an iodine atom or —$NR_{b4}R_{b5}$, in which $R_{b4}$ is hydrogen or $C_1$–$C_5$-alkyl, and $R_{b5}$ is monochloroacetyl, or $R_{b4}$ is methyl, n-propyl, isopropyl, n-butyl, sec-butyl, tert-butyl or isobutyl, and $R_{b5}$ is dichloroacetyl.

To be emphasised amongst these compounds are especially the compounds of the formula Ic embraced by the formula Ib

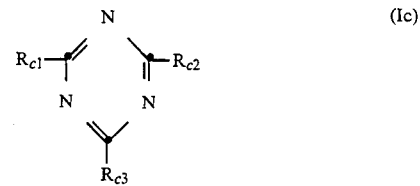
(Ic)

wherein one of the substituents $R_{c1}$, $R_{c2}$ and $R_{c3}$ is $C_1$–$C_5$-alkyl which is unsubstituted or monosubstituted by $C_3$–$C_6$-cycloalkyl or mono- or polysubstituted by halogen, or is $C_3$–$C_6$-cycloalkyl which is unsubstituted or mono- or polysubstituted by halogen; a further of the substituents $R_{c1}$, $R_{c2}$ and $R_{c3}$ is n-pentyl or an isomer thereof, $C_1$–$C_5$-alkyl which is monosubstituted by $C_3$–$C_6$-cycloalkyl, or is $C_4$–$C_5$-alkyl which is mono- or polysubstituted by halogen, or is $C_3$–$C_6$-cycloalkyl which is unsubstituted or mono- or polysubstituted by halogen, or is an iodine atom; and the third of the substituents $R_{c1}$, $R_{c2}$ and $R_{c3}$ is $C_1$–$C_5$-alkyl which is unsubstituted or monosubstituted by $C_3$–$C_6$-cycloalkyl or mono- or polysubstituted by fluorine, bromine or iodine, or is $C_2$–$C_5$-alkyl which is mono- or polysubstituted by chlorine, or is chloromethyl, dichloromethyl, $C_3$–$C_6$-cycloalkyl which is unsubstituted or mono- or polysubstituted by halogen, with the proviso that at least one of the substituents $R_{c1}$, $R_{c2}$ and $R_{c3}$ is cycloalkyl which is unsubstituted or mono- or polysubstituted by halogen.

Compounds of the formua Ic which are of particular interest are those in which the cycloalkyl group is an unsubstituted cyclopropyl group.

The compounds of the formula I can be produced by methods known per se, for example by condensation of correspondingly substituted nitriles, or by exchange of substituents on the triazine ring. Thus, for example, triazines substituted by trichloromethyl or methoxy can be converted by treatment with ammonia into the corresponding triazines substituted by amino. Compounds in which $R_5$, $R_{a5}$ or $R_{b5}$ is mono- or dichloroacetyl can be produced by reacting a corresponding triazine derivative substituted by amino or alkylamino with mono- or dichloroacetyl chloride.

EXAMPLE 1

2-(3-Chloro-n-propyl)-4-methyl-6-(trichloromethyl)-1,3,5-triazine (compound No. 7)

A solution of 5 g of 4-chloro-n-butyronitrile in 15 g of trichloroacetonitrile is saturated at room temperature with hydrochloric acid, and the reaction mixture is left to stand for 14 hours at room temperature. The occurring precipitate is filtered off with suction, and is suspended together with 8 g of acetimidoethyl ester hydrochloride in 50 ml of acetronitrile. To this suspension are added dropwise 10 g of triethylamine and, after the exothermic reaction has subsided, the mixture is stirred for 1 hour at room temperature. The precipitated triethylammonium hydrochloride is subsequently separated by filtration and the reaction mixture is concentrated by evaporation. The crude product is chromatographed on silicon dioxide (elution with ether/hexane 1:10) to yield 4.5 g of 2-(3-chloro-n-propyl)-4-methyl-6-(trichloromethyl)-1,3,5-triazine as a slightly yellow oil, $n_D^{22} = 1.5290$.

EXAMPLE 2

2-Cyclopropyl-4,6-bis(trichloromethyl)-1,3,5-triazine (compound No. 18).

760 g of trichloroacetonitrile are cooled to −15° C., and hydrogen chloride gas is blown through the solution until saturation is reached. There are then slowly added, with cooling and the addition of hydrogen chloride gas, 230 g of cyclopropylnitrile, the temperature not being allowed to exceed −10° C. The cooling bath is removed, and the reaction mixture is stirred at room temperature until the temperature has risen to 15° C. Upwards of 10° C. there commences, with a slightly exothermic reaction, the evolution of hydrogen chloride, which finally ceases after 20 hours' stirring at 15°–20° C. To the reaction mixture are subsequently added 1.5 liters each of ether and hexane, and the whole is thoroughly stirred and afterwards filtered. The filtrate is concentrated by evaporation; the residue is then boiled up in 700 ml of hexane, again filtered and the filtrate is concentrated afresh by evaporation. The residue is recrystallised from methanol to thus obtain 350 g of the above triazine, m.p. 100°–102° C.

EXAMPLE 3

2-Amino-4-cyclopropyl-6-trichloromethyl-1,3,5-triazine (compound No. 21)

71.2 g of 2-cyclopropyl-4,6-bis-trichloromethyl-1,3,5-triazine are dissolved in 70 ml of tetrahydrofuran, and, with stirring, 300 ml of concentrated aqueous ammonia solution are added at room temperature. The mixture is stirred for 30 minutes; it is then diluted with water, and the formed emulsion is extracted with ether. The ether phases are collected, dried, filtered and subsequently concentrated by evaporation. The yield is 48 g of the crystalline title product, m.p. 111°–114° C.

EXAMPLE 4

2-Amino-4-(3-chloro-n-propyl)-6-trichloromethyl-1,3,5-triazine (compound No. 12)

102.3 g of 2-(3-chloro-n-propyl)-4,6-bis-(trichloromethyl)-1,3,5-triazine are dissolved in 100 ml of tetrahydrofuran, and to this solution are added at room temperature, with stirring, 400 ml of concentrated aqueous ammonia solution. After 30 minutes, 500 ml of water are addded, and the reaction mixture is extracted twice with 100 ml of ether each time. The ether phases are dried over magnesium sulfate, filtered, and concentrated by evaporation to leave 68.3 g of title product in the form of light-brown oil.

EXAMPLE 5

2-(3-Chloro-n-propyl)-4,6-bis(trichloromethyl)-1,3,5-triazine (compound No. 4)

At a temperature of −20° C., gaseous hydrogen chloride is blown through a solution of 103 g of 4-chlorobutyronitrile in 298 g of trichloroacetonitrile until the solution is saturated. It is then slowly heated, with stirring, to room temperature, in the course of which only a relatively slight evolution of gas occurs and a crystalline precipitate is formed. There is added one liter of toluene, and the reaction mixture is stirred at 85° C. until no further HCl gas is evolved. Stirring is discontinued, the solution is allowed to cool, and the clear solution is separated by decanting from the sludge which has settled. The solution is concentrated by evaporation, and the oil which remains is distilled under high vacuum to yield 294 g of the title product; b.p. 150°–160° C./0.2 mbar; refractive index $n_D^{27}$: 1.5498.

By a method analogous to one of those described in the foregoing, there can also be produced the following compounds of the formula I, listed in Table 1 together with the compounds of the above Examples.

TABLE 1

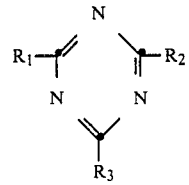

| Compound No. | $R_1$ | $R_2$ | $R_3$ | Physical constants |
|---|---|---|---|---|
| 1 | CCl$_3$ | CCl$_3$ | CH$_3$ | m.p. 93–94° C. |
| 2 | CCl$_3$ | NHC$_2$H$_5$ | cyclopropyl | m.p. 47–49° C. |
| 3 | CH$_3$ | NH—CO—CHCl$_2$ | CH$_2$CH$_2$CH$_2$Cl | |

TABLE 1-continued

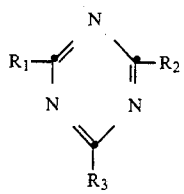

| Compound No. | R₁ | R₂ | R₃ | Physical constants |
|---|---|---|---|---|
| 4 | CCl₃ | CCl₃ | CH₂CH₂CH₂Cl | $n_D^{27} = 1,5498$ |
| 5 | CCl₃ | NHCH₃ | cyclopropyl | m.p. 100–102° C. |
| 6 | Cl | N(C₂H₅)—CO—CHCl₂ | NHC₂H₅ | m.p. 99–101° C. |
| 7 | CCl₃ | CH₃ | CH₂CH₂CH₂Cl | $n_D^{22} = 1,5290$ |
| 8 | CCl₃ | NHnC₃H₇ | cyclopropyl | m.p. 66–68° C. |
| 9 | CCl₃ | CCl₃ | CH₂Cl | m.p. 59–61° C. |
| 10 | CH₃ | NH—CO—CH₂Cl | CH₂CH₂CH₂Cl | |
| 11 | CCl₃ | C₂H₅ | CH₂CH₂CH₂Cl | |
| 12 | CCl₃ | NH₂ | CH₂CH₂CH₂Cl | oil |
| 13 | CCl₃ | CCl₃ | CH₂CH₂CH₂CH₂Cl | oil |
| 14 | CCl₃ | N(CH₃)₂ | cyclopropyl | m.p. 59–61° C. |
| 15 | CH₃ | NH₂ | CH₃ | |
| 16 | CCl₃ | cyclopropyl | CH₂CH₂CH₂Cl | $n_D^{22} = 1,5325$ |
| 17 | CH₃ | NH₂ | cyclopropyl | |
| 18 | CCl₃ | CCl₃ | cyclopropyl | m.p. 100–102° C. |
| 19 | CCl₃ | NHisoC₃H₇ | cyclopropyl | oil |
| 20 | CCl₃ | nC₃H₇ | CH₂CH₂CH₂Cl | |
| 21 | CCl₃ | NH₂ | cyclopropyl | m.p. 111–114° C. |
| 22 | CCl₃ | NH₂ | CH₂Cl | m.p. 109–113° C. |
| 23 | CCl₃ | NH₂ | CCl₃ | m.p. 160–161° C. |
| 24 | CCl₃ | CCl₃ | Cl | m.p. 54–57° C. |
| 25 | CCl₃ | NHC₂H₅ | CCl₃ | m.p. 77–79° C. |
| 26 | CCl₃ | CCl₃ | CCl₃ | solid |
| 27 | CCl₃ | NHCH₃ | CH₃ | m.p. 125–131° C. |
| 28 | CCl₃ | NH₂ | CH₃ | m.p. 154–157° C. |
| 29 | CCl₃ | CCl₃ | isoC₃H₇ | oil |
| 30 | CCl₃ | CCl₃ | C₂H₅ | m.p. 37–39° C. |
| 31 | CHCl₂ | NH₂ | CH₃ | m.p. 114–115° C. |
| 32 | CHCl₂ | NH₂ | cyclopropyl | m.p. 114–116° C. |
| 33 | CHCl₂ | NH—CO—CHCl₂ | CH₃ | |
| 34 | CHCl₂ | NH—CO—CH₂Cl | cyclopropyl | |
| 35 | CHCl₂ | NH—CO—CH₂Cl | CH₃ | |
| 36 | CHCl₂ | NH—CO—CHCl₂ | cyclopropyl | |

Formulation Examples for Liquid Active Ingredients of the Formula I (%=Percent by Weight)

| 6. Emulsion concentrates | a | b | c |
|---|---|---|---|
| active ingredient from Table 1 | 25% | 40% | 50% |
| calcium dodecylbenzenesulfonate | 5% | 8% | 6% |
| castor oil-polyethylene gycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 7. Solutions | a | b | c | d |
|---|---|---|---|---|
| active ingredient from Table 1 | 80% | 10% | 5% | 95% |
| ethylene glycol-monomethyl ether | 20% | — | — | — |
| polyethylene glycol M.W. 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 8. Granulates | a | b |
|---|---|---|
| active ingredient from Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 9. Dusts | a | b |
|---|---|---|
| active ingredient from Table 1 | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

Formulation Examples for Solid Active Ingredients of the Formula I (%=Percent by Weight)

| 10. Wettable powders | a | b | c |
|---|---|---|---|
| active ingredient from Table 1 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |

| 10. Wettable powders | a | b | c |
|---|---|---|---|
| octylphenolpolyethylene glycol ether (7-8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. Wettable powders which can be diluted with water to give suspensions of the required concentration are obtained.

| 11. Emulsion concentrate | |
|---|---|
| active ingredient from Table 1 | 10% |
| octylphenolpolyethylene glycol ether (4-5 mols of ethylene oxide) | 3% |
| calcium dodecylbenzenesulfonate | 3% |
| castor oil polyglycol ether (35 mols of ethylene oxide) | 4% |
| cyclohexanone | 30% |
| xylene mixture | 50% |

Emulsions of the required concentration can be obtained from this concentrate by dilution with water.

| 12. Dusts | a | b |
|---|---|---|
| active ingredient from Table 1 | 5% | 8% |
| talcum | 95% | — |
| kaolin | — | 92% |

Dusts ready for use are obtained by mixing the active ingredient with the carriers and grinding the mixture in a suitable mill.

| 13. Exturder granulate | |
|---|---|
| active ingredient from Table 1 | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded and subsequently dried in a stream of air.

| 14. Coated granulate | |
|---|---|
| active ingredient from Table 1 | 3% |
| polyethylene glycol (M.W. 200) | 3% |
| kaolin | 94% |

The finely ground active ingredient is evenly applied, in a mixer, to the kaolin moistened with polyethylene glycol. Dustfree coated granules are obtained in this manner.

| 15. Suspension concentrate | |
|---|---|
| active ingredient from Table 1 | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |

| 15. Suspension concentrate | |
|---|---|
| water | 32% |

The finely ground active ingredient is intimately mixed with the additives. There is thus obtained a suspension concentrate from which can be produced, by dilution with water, suspensions of the concentration required.

Formulation Examples for Active-Ingredient Mixtures (Liquid) (%=Percent by Weight)

| 16. Emulsion concentrates | a | b | c |
|---|---|---|---|
| active ingredient mixture: antidote from Table 1 and one of the herbicides H-1 to H-61 in the ratio of 1:1 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 17. Emulsion concentrates | a | b | c |
|---|---|---|---|
| active-ingredient mixture: antidote from Table 1 and one of the herbicides H-1 to H-61 in the ratio of 1:3 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 18. Emulsion concentrates | a | b | c |
|---|---|---|---|
| active ingredient mixture: antidote from Table 1 and one of the herbicides H-1 to H-61 in the ratio of 2:1 | 25% | 40% | 50% |
| calcium dodecylbenzensulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 19. Emulsion concentrates | a | b | c |
|---|---|---|---|
| active-ingredient mixture: antidote from Table 1 and N—(1-isopropyl-2-methyl-1-propen-1-yl)-N—(2-methoxyethyl)-chloroacetamide in the ratio of 1:1 | 25% | 40% | 50% |
| calcium dodecylbenzenesulfonate | 5% | 8% | 6% |
| castor oil-polyethylene glycol ether (36 mols of ethylene oxide) | 5% | — | — |

-continued

| 19. Emulsion concentrates | a | b | c |
|---|---|---|---|
| tributylphenol-polyethylene glycol ether (30 mols of ethylene oxide) | — | 12% | 4% |
| cyclohexanone | — | 15% | 20% |
| xylene mixtures | 65% | 25% | 20% |

Emulsions of any required concentration can be produced from concentrates of this type by dilution with water.

| 20. Emulsion concentrates | a | b | c |
|---|---|---|---|
| active-ingredient mixture: antidote from Table 1 and N—(1-isopropyl-2-methyl-1-propen-1-yl)-N—(2-methoxyethyl)-chloroacetamide in the ratio of 1:3 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 21. Solutions | a | b | c | d |
|---|---|---|---|---|
| active-ingredient mixture: antidote from Table 1 and one of the herbicides H-1 to H-61 in the ratio of 1:4 | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 22. Solutions | a | b | c | d |
|---|---|---|---|---|
| active ingredient mixture: antidote from Table 1 and one of the herbicides H-1 to H-61 in the ratio of 5:2 | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 23. Solutions | a | b | c | d |
|---|---|---|---|---|
| active ingredient mixture: antidote from Table 1 and one of the herbicides H-1 to H-61 in the ratio of 1:1 | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 24. Solutions | a | b | c | d |
|---|---|---|---|---|
| active-ingredient mixture: antidote from Table 1 and N—(1-isopropyl-2-methyl-1-propen-1-yl)-N—(2-methoxyethyl)-chloroacetamide in the ratio of 1:1 | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 25. Solutions | a | b | c | d |
|---|---|---|---|---|
| active-ingredient mixture: antidote from Table 1 and N—(1-isopropyl-2-methyl-1-propen-1-yl)-N—(2-methoxyethyl)-chloroacetamide in the ratio of 1:4 | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 26. Granulates | a | b |
|---|---|---|
| active-ingredient mixture: antidote from Table 1 and one of the herbicides H-1 to H-61 in the ratio of 1:1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 27. Granulates | a | b |
|---|---|---|
| active-ingredient mixture: antidote from Table 1 and N—(1-isopropyl-2-methyl-1-propen-1-yl)-N—(2-methoxyethyl)-chloroacetamide in the ratio of 1:1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 28. Dusts | a | b |
|---|---|---|
| active-ingredient mixture: antidote from Table 1 and one of the herbicides H-1 to H-61 in the ratio of 1:1 | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

Formulation Examples for Active-Ingredient Mixtures
(Solid) (% = Percent by Weight)

| 29. Wettable powders | a | b | c |
|---|---|---|---|
| active-ingredient mixture: antidote from Table 1 and one of the herbicides H-1 to H-61 in the ratio of 1:1 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. Wettable powders which can be diluted with water to give suspensions of the required concentration are obtained.

| 30. Wettable powders | a | b | c |
|---|---|---|---|
| active-ingredient mixture: antidote from Table 1 and one of the herbicides H-1 to H-61 in the ratio of 1:4 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. Wettable powders which can be diluted with water to give suspensions of the required concentration are obtained.

| 31. Wettable powders | a | b | c |
|---|---|---|---|
| active-ingredient mixture: antidote from Table 1 and one of the herbicides H-1 to H-61 in the ratio of 3:1 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. Wettable powders which can be diluted with water to give suspensions of the required concentration are obtained.

| 32. Emulsion concentrate | |
|---|---|
| active-ingredient mixture: antidote from Table 1 and one of the herbicides H-1 to H-61 in the ratio of 1:1 | 10% |
| octylphenol polyethylene glycol ether (4–5 mols of ethylene oxide) | 3% |
| calcium dodecylbenzenesulfonate | 3% |
| castor oil-polyglycol ether (35 mols of ethylene oxide) | 4% |
| cyclohexanone | 30% |
| xylene mixture | 50% |

Emulsions of the required concentration can be obtained from this concentrate by dilution with water.

| 33. Emulsion concentrate | |
|---|---|
| active-ingredient mixture: antidote from Table 1 and one of the herbicides H-1 to H-61 in the ratio of 5:2 | 10% |
| octylphenol polyethylene glycol ether (4–5 mols of ethylene oxide) | 3% |
| calcium dodecylbenzenesulfonate | 3% |
| castor oil-polyglycol ether (35 mols of ethylene oxide) | 4% |
| cyclohexanone | 30% |
| xylene mixture | 50% |

Emulsions of the required concentration are obtained from this concentrate by dilution with water.

| 34. Emulsion concentrate | |
|---|---|
| active-ingredient mixture: antidote from Table 1 and one of the herbicides H-1 to H-61 in the ratio of 1:4 | 10% |
| octylphenol polyethylene glycol ether (4–5 mols of ethylene oxide) | 3% |
| calcium dodecylbenzenesulfonate | 3% |
| castor oil-polyglycol ether (35 mols of ethylene oxide) | 4% |
| cyclohexanone | 30% |
| xylene mixture | 50% |

Emulsions of the required concentration can be obtained from this concentrate by dilution with water.

| 35. Dusts | a | b |
|---|---|---|
| active-ingredient mixture: antidote from Table 1 and one of the herbicides H-1 to H-61 in the ratio of 1:1 | 5% | 8% |
| talcum | 95% | — |
| kaolin | — | 92% |

Dusts ready for use are obtained by mixing the active ingredient with the carriers and grinding the mixture in a suitable mill.

| 36. Extruder granulate | |
|---|---|
| active-ingredient mixture: antidote from Table 1 and one of the herbicides H-1 to H-61 in the ratio of 1:1 | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded and subsequently dried in a stream of air.

| 37. Coated granulate | |
|---|---|
| active-ingredient mixture: antidote from Table 1 and one of the herbicides H-1 to H-61 in the ratio of 1:1 | 3% |
| polyethylene glycol (M.W. 200) | 3% |
| kaolin | 94% |

The finely ground active ingredient is evenly applied, in a mixer, to the kaolin moistened with polyethylene glycol. Dustfree coated granules are obtained in this manner.

| 38. Suspension concentrate | |
| --- | --- |
| active-ingredient mixture: antidote from Table 1 and one of the herbicides H-1 to H-61 in the ratio of 1:1 | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of the concentration required.

| 39. Suspension concentrate | |
| --- | --- |
| active-ingredient mixture: antidote from Table 1 and one of the herbicides H-1 to H-61 in the ratio of 1:4 | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of the concentration required.

| 40. Suspension concentrate | |
| --- | --- |
| active-ingredient mixture: antidote from Table 1 and one of the herbicides H-1 to H-61 in the ratio of 3:1 | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of the concentration required.

BIOLOGICAL EXAMPLES

Example 41

Tank mixture in the pre-emergence process on maize. Plastics containers (length×width×height=25×17×12 cm) are filled with sandy loam soil, into which are sown maize seeds of the LG 5 variety. After the seeds have been covered with soil, 2-(3-chloro-n-propyl)-4-methyl-6-(trichloromethyl)-1,3,5-triazine as antidote and the herbicide 2-chloro-2',6'-dimethyl-N-(2-methoxy-1-methylethyl)-acetanilide are sprayed together in dilute solution as a tank mixture onto the surface of the soil. The protective action of the antidote is estimated in percent 21 days after application. The plants treated with the herbicide alone and the completely untreated control plants provide reference data. With applied amounts corresponding for the antidote to 1.5 kg/hectare and for the herbicide to 6.0 kg/hectare, a relative protective action of 75% is achieved.

Example 42

Tank mixture in the pre-emergence process on maize. Maize seeds of the "LG 5" variety are sown, in a greenhouse, in plastics pots (upper diameter 11 cm) each containing 0.5 liter of sandy loam soil. After the seeds have been covered with soil, the substance to be tested as safener and the herbicide, N-chloroacetyl-N-(2-methoxy-1-methylethyl)-2,6-dimethylaniline, are applied together as a tank mixture, which corresponds to 550 l/ha and to herbicide amounts of 4 kg and 6 kg/ha, respectively, in the pre-emergence process to the surface of the soil. The protective action of the safener is assessed 21 days after application. Reference values are provided by the maize treated with the herbicide alone and by the completely untreated control plants. The results are summarised in Tables 2 and 3.

TABLE 2

| Herbicide: H-44, 4 kg of active ingredient per hectare | | | | |
| --- | --- | --- | --- | --- |
| Safener No. | Relative protective action in % with an applied amount of safener of | | | |
| | 2 kg/ha | 1 kg/ha | 0.5 kg/ha | 0.25 kg/ha |
| 1 | 50 | 50 | 50 | 0 |
| 7 | 50 | 63 | 50 | 50 |
| 16 | 13 | 13 | 25 | 38 |
| 29 | 63 | 75 | 63 | 63 |
| 30 | 63 | 50 | 50 | 50 |

TABLE 3

| Herbicide: H-44, 6 kg of active ingredient per hectare | | | | |
| --- | --- | --- | --- | --- |
| Safener No. | Relative protective action in % with an applied amount of safener of | | | |
| | 3 kg/ha | 1.5 kg/ha | 0.75 kg/ha | 0.375 kg/ha |
| 1 | 50 | 50 | 63 | 13 |
| 7 | 63 | 63 | 63 | 50 |
| 16 | 13 | 13 | 13 | 0 |
| 29 | 63 | 75 | 75 | 75 |
| 30 | 38 | 38 | 50 | 63 |

Example 43

Tank mixture in the pre-emergence process on maize. Plastics containers (length×width×height=25×17×12 cm) are filled with sandy loam soil, into which are sown the maize seeds. After the seeds have been covered with soil, the substance to be tested as safener and the herbicide, N-chloroacetyl-N-(2-methoxy-1-methylethyl)-2,6-dimethylaniline, are sprayed together in dilute solution as a tank mixture onto the surface of the soil, the amounts of herbicide corresponding to 4 kg/ha and 6 kg/ha, respectively. The protective action of the safener is assessed 21 days after application. Reference values are provided by the plants treated with the herbicide alone and by the completely untreated control plants. The results are summarised in the following Tables 4 and 5.

TABLE 4

Herbicide: H-44, 4 kg of active ingredient per hectare

| Safener No. | Relative protective action in % with an applied amount of safener in kg/ha of | | | | |
|---|---|---|---|---|---|
| | 2 | 1 | 0.5 | 0.333 | 0.25 |
| 1 | 63 | 63 | 50 | 13 | 25 |
| 7 | 63 | 63 | 50 | 38 | 13 |

TABLE 5

Herbicide: H-44, 6 kg of active ingredient per hectare

| Safener No. | Relative protective action in % with an applied amount of safener in kg/ha of | | | | |
|---|---|---|---|---|---|
| | 3 | 1.5 | 0.75 | 0.5 | 0.375 |
| 1 | 75 | 50 | 38 | 25 | 25 |
| 7 | 75 | 63 | 63 | 38 | 38 |

Example 44

Separate application of safener and herbicide in the pre-emergence process on maize.

Plastics pots (upper diameter 9 cm, content 315 ml) are filled with sandy-clayey loam soil. Maize seeds of the "LG 5" variety are sown therein, covered with soil and watered. The substance to be tested as safener is dissolved in water, and the solution is sprayed, in an amount corresponding to 550 l/ha and to a safener amount of 1.5 kg/ha, onto the surface of the soil. The herbicide, N-chloroacetyl-N-(2-methoxy-1-methylethyl)-2,6-dimethylaniline, is subsequently dissolved in water and the solution applied in the same manner, the herbicide amount corresponding to 6 kg/ha. The test plants are cultivated in a greenhouse under the following conditions: 13 hours of light (24°-26° C.), 11 hours of darkness (20°-22° C.) and about 40-60% relative air humidity. The protective action of the safener is estimated in percent two weeks after application. Reference values are provided by plants treated with the herbicide alone and by completely untreated control plants. The results are summarised in Table 6.

TABLE 6

| Safener No. | Relative protective action in % |
|---|---|
| 27 | 13 |
| 18 | 50 |
| 4 | 50 |
| 8 | 13 |
| 21 | 13 |
| 1 | 25 |
| 9 | 13 |
| 22 | 25 |
| 28 | 38 |
| 14 | 13 |
| 7 | 38 |
| 23 | 50 |
| 16 | 75 |
| 29 | 63 |
| 30 | 63 |
| 31 | 63 |
| 32 | 38 |

Example 45

Separate application of safener and herbicide in the pre-emergence process on sorghum.

Plastics pots (upper diameter 6.5 cm, content 165 ml) are filled with sandy-clayey loam soil. Sorghum seeds of the "Funk G-623" variety are sown therein, covered with soil and watered. The substance to be tested as safener is dissolved in water, and the solution is sprayed, in an amount corresponding to 550 l/ha and to a safener amount of 1.5 kg/ha, onto the surface of the soil. The herbicide, N-chloroacetyl-N-(2-methoxy-1-methylethyl)-2-ethyl-6-methylaniline, is subsequently dissolved in water and the solution applied in the same manner, the amount of herbicide corresponding to 1.5 kg/ha. The test plants are cultivated in a greenhouse under the following conditions: 13 hours of light (24°-26° C.), 11 hours of darkness (20°-22° C.) and about 40-60% relative air humidity. The protective action of the safener is assessed in percent two weeks after application. Reference values are provided by plants treated with the herbicide alone and by completely untreated control plants. The results are summarised in Table 7.

TABLE 7

| Safener No. | Relative protective action in % |
|---|---|
| 8 | 50 |
| 31 | 38 |

What is claimed is:

1. A process for the protection of maize and sorghum plants against the harmful effects of herbicidal chloroacetanilides and chloroacetamides, which process comprises treating these plants, parts of these plants or cultivated areas for these plants with a compound of the formula I

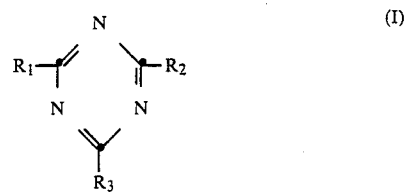

wherein
R$_1$, R$_2$ and R$_3$ independently of one another are each C$_1$-C$_5$-alkyl which is unsubstituted or monosubstituted by C$_3$-C$_6$-cycloalkyl, or mono- or polysubstituted by halogen, or is C$_3$-C$_6$-cycloalkyl which is unsubstituted or mono- or polysubstituted by halogen, or one of the substituents R$_1$, R$_2$ and R$_3$ is also halogen or —NR$_4$R$_5$, in which R$_4$ is hydrogen or C$_1$-C$_5$-alkyl and R$_5$ is hydrogen, C$_1$-C$_5$-alkyl, monochloroacetyl or dichloroacetyl, or with a composition containing a compound of the formula I.

2. A process according to claim 1, which process comprises applying a compound of the formula I in which two of the substituents R$_1$, R$_2$ and R$_3$ independently of one another are each C$_1$-C$_5$-alkyl which is unsubstituted or monosubstituted by C$_3$-C$_6$-cycloalkyl or mono- or polysubstituted by halogen, or are C$_3$-C$_6$-cycloalkyl which is unsubstituted or mono- or polysubstituted by halogen, or one of the substituents is also halogen, and the third substituent is C$_3$-C$_6$-cycloalkyl.

3. A process according to claim 2, which process comprises applying a compound of the formula I in which two of the substituents R$_1$, R$_2$ and R$_3$ independently of one another are each C$_1$-C$_5$-alkyl which is unsubstituted or monosubstituted by cyclopropyl or mono- or polysubstituted by halogen, or are cyclopropyl, or one of the substituents is also halogen, and the third substituent is cyclopropyl.

4. A process according to claim 1 for the protection of maize and sorghum plants against the harmful effects of chloroacetanilides.

5. A process according to claim 4 for the protection of maize and sorghum plants against the harmful effects of chloroacetanilides of the formula II

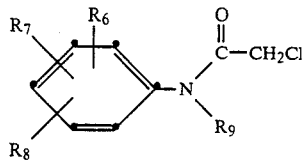

wherein
$R_6$ is hydrogen, $C_1$-$C_4$-alkyl, methoxy or chlorine, $R_7$ is hydrogen or $C_1$-$C_3$-alkyl, and $R_8$ is hydrogen, methyl or ethyl, with the proviso that $R_6$, $R_7$ and $R_8$ together do not contain more than 6 carbon atoms, and $R_9$ is ethyl, isopropyl, 1-methyl-2-methoxyethyl, —$CH_2$—$R_{10}$, —$CH(CH_3)$—$R_{11}$, —$CH_2$—$CH(R_{12})$—$R_{13}$, —$CH(CH_3)$—$CH(R_{14})$—$R_{15}$, $C_3$-$C_4$-alkynyl or 5-methyl-1,3,4-oxadiazol-2-yl, in which $R_{10}$ is $C_1$-$C_4$-alkoxy, $C_1$-$C_3$-alkoxycarbonyl, dimethylaminocarbonyl, 2-propynylaminocarbonyl, benzoyl, 4-chlorobenzoyl, cyano, 2-furanyl, 2-tetrahydrofuranyl, 1,3-dioxolan-2-yl, 1,3-dioxan-2-yl, 1H-pyrazol-1-yl, 3,5-dimethyl-1H-pyrazol-1-yl, 1H-1,2,4-triazol-1-yl, 1-methyl-5-methylthio-1,3,4-triazol-2-yl or —$P(O)(OR_{16})(OR_{17})$, in which $R_{16}$ and $R_{17}$ independently of one another are each methyl or ethyl, $R_{11}$ is methoxycarbonyl or 1,3-dioxolan-2-yl, $R_{12}$ is hydrogen, and $R_{13}$ is $C_1$-$C_4$-alkoxy or allyloxy, or $R_{12}$ is methyl and $R_{13}$ is $C_1$-$C_2$-alkoxy, or $R_{12}$ and $R_{13}$ are ethoxy and $R_{14}$ is hydrogen and $R_{15}$ is $C_1$-$C_2$-alkoxy, or $R_{14}$ is methyl and $R_{15}$ is methoxy.

6. A composition for the protection of maize and sorghum plants against the harmful effects of chloroacetanilides and chloroacetamides, which composition contains a compound of the formula I

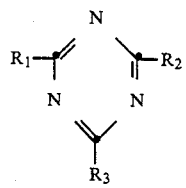

wherein
$R_1$, $R_2$ and $R_3$ independently of one another are each $C_1$-$C_5$-alkyl which is unsubstituted or monosubstituted by $C_3$-$C_6$-cycloalkyl, or mono- or polysubstituted by halogen, or is $C_3$-$C_6$-cycloalkyl which is unsubstituted or mono- or polysubstituted by halogen, or one of the substituents $R_1$, $R_2$ and $R_3$ is also halogen or —$NR_4R_5$, in which $R_4$ is hydrogen or $C_1$-$C_5$-alkyl and $R_5$ is hydrogen, $C_1$-$C_5$-alkyl, monochloroacetyl or dichloroacetyl.

7. A composition according to claim 6, wherein in the compound of the formula I two of the substituents $R_1$, $R_2$ and $R_3$ independently of one another are each $C_1$-$C_5$-alkyl which is unsubstituted or monosubstituted by $C_3$-$C_6$-cycloalkyl or mono- or polysubstituted by halogen, or are $C_3$-$C_6$-cycloalkyl which is unsubstituted or mono- or polysubstituted by halogen, or one of the substituents is also halogen, and the third substituent is $C_3$-$C_6$-cycloalkyl.

8. A composition according to claim 7, wherein in the compound of the formula I two of the substituents $R_1$, $R_2$ and $R_3$ independently of one another are each $C_1$-$C_5$-alkyl which is unsubstituted or monosubstituted by cyclopropyl or mono- or polysubstituted by halogen, or are cyclopropyl, or one of the substituents is also halogen, and the third substituent is cyclopropyl.

9. A composition according to claim 6, which contains a herbicidal chloroacetanilide.

10. A composition according to claim 9, which composition contains a chloroacetanilide of the formula II

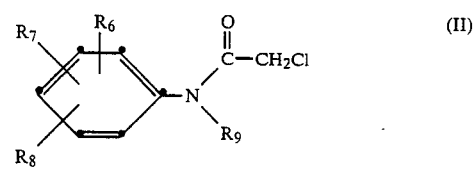

wherein
$R_6$ is hydrogen, $C_1$-$C_4$-alkyl, methoxy or chlorine, $R_7$ is hydrogen or $C_1$-$C_3$-alkyl, and $R_8$ is hydrogen, methyl or ethyl, with the proviso that $R_6$, $R_7$ and $R_8$ together do not contain more than 6 carbon atoms, and $R_9$ is ethyl, isopropyl, 1-methyl-2-methoxyethyl, —$CH_2$—$R_{10}$, —$CH(CH_3)$—$R_{11}$, —$CH_2$—$CH(R_{12})$—$R_{13}$, —$CH(CH_3)$—$CH(R_{14})$—$R_{15}$, $C_3$-$C_4$-alkynyl or 5-methyl-1,3,4-oxadiazol-2-yl, in which $R_{10}$ is $C_1$-$C_4$-alkoxy, $C_1$-$C_3$-alkoxycarbonyl, dimethylaminocarbonyl, 2-propynylaminocarbonyl, benzoyl, 4-chlorobenzoyl, cyano, 2-furanyl, 2-tetrahydrofuranyl, 1,3-dioxolan-2-yl, 1,3-dioxan-2-yl, 1H-pyrazol-1-yl, 3,5-dimethyl-1H-pyrazol-1-yl, 1H-1,2,4-triazol-1-yl, 1-methyl-5-methylthio-1,3,4-triazol-2-yl or —$P(O)(OR_{16})(OR_{17})$, in which $R_{16}$ and $R_{17}$ independently of one another are each methyl or ethyl, $R_{11}$ is methoxycarbonyl or 1,3-dioxolan-2-yl, $R_{12}$ is hydrogen, and $R_{13}$ is $C_1$-$C_4$-alkoxy or allyloxy, or $R_{12}$ is methyl and $R_{13}$ is $C_1$-$C_2$-alkoxy, or $R_{12}$ and $R_{13}$ are ethoxy and $R_{14}$ is hydrogen and $R_{15}$ is $C_1$-$C_2$-alkoxy, or $R_{14}$ is methyl and $R_{15}$ is methoxy.

* * * * *